US012766182B2

(12) United States Patent
Weiss et al.

(10) Patent No.: US 12,766,182 B2
(45) **Date of Patent: *Oct. 20, 2026**

(54) TOPICAL CYCLOSPORINE-CONTAINING FORMULATIONS AND USES THEREOF

(71) Applicant: SUN PHARMACEUTICAL INDUSTRIES LIMITED, Mumbai (IN)

(72) Inventors: Sidney L. Weiss, Randolph, NJ (US); Ashim K. Mitra, Overland Park, KS (US); Eugene J. Mcnally, Fitchburg, WI (US)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,539

(22) Filed: Feb. 28, 2024

(65) Prior Publication Data

US 2024/0197818 A1 Jun. 20, 2024

Related U.S. Application Data

(60) Continuation of application No. 17/935,177, filed on Sep. 26, 2022, now Pat. No. 11,951,153, which is a continuation of application No. 17/143,863, filed on Jan. 7, 2021, now abandoned, which is a division of application No. 16/079,928, filed as application No. PCT/US2017/020008 on Feb. 28, 2017, now Pat. No. 10,918,694.

(60) Provisional application No. 62/311,177, filed on Mar. 21, 2016, provisional application No. 62/302,730, filed on Mar. 2, 2016, provisional application No. 62/302,058, filed on Mar. 1, 2016, provisional application No. 62/301,576, filed on Feb. 29, 2016.

(51) Int. Cl.

| | |
|---|---|
| ***A61K 9/107*** | (2006.01) |
| ***A61K 9/00*** | (2006.01) |
| ***A61K 31/202*** | (2006.01) |
| ***A61K 38/13*** | (2006.01) |
| ***A61K 47/10*** | (2017.01) |
| ***A61K 47/44*** | (2017.01) |
| ***A61P 27/02*** | (2006.01) |

(52) U.S. Cl.

CPC ............ *A61K 38/13* (2013.01); *A61K 9/0048* (2013.01); *A61K 9/107* (2013.01); *A61K 31/202* (2013.01); *A61K 47/10* (2013.01); *A61K 47/44* (2013.01); *A61P 27/02* (2018.01)

(58) Field of Classification Search

None

See application file for complete search history.

(56) References Cited

U.S. PATENT DOCUMENTS

| | | | |
|---|---|---|---|
| 5,484,597 | A | 1/1996 | Slavtcheff et al. |
| 5,843,891 | A | 12/1998 | Sherman et al. |
| 5,951,971 | A | 9/1999 | Kawashima et al. |
| 5,998,365 | A | 12/1999 | Sherman et al. |
| 6,071,958 | A | 6/2000 | Jimenez-Bayardo et al. |
| 7,060,672 | B2 | 6/2006 | Naicker et al. |
| 7,087,237 | B2 | 8/2006 | Peyman |
| 7,833,966 | B2 | 11/2010 | Peyman |
| 8,435,544 | B2 | 5/2013 | Mitra et al. |
| 8,535,694 | B2 | 9/2013 | Mitra et al. |
| 8,796,221 | B2 | 8/2014 | Wu et al. |
| 8,828,412 | B2 | 9/2014 | Yu et al. |
| 8,980,839 | B2 | 3/2015 | Mitra et al. |
| 9,017,725 | B2 | 4/2015 | Mitra et al. |
| 9,770,447 | B2 | 9/2017 | Ostrow et al. |
| 9,937,225 | B2 | 4/2018 | Mitra et al. |
| 10,265,375 | B2 | 4/2019 | Mitra et al. |
| 10,441,630 | B2 | 10/2019 | Mitra et al. |
| 10,918,694 | B2 | 2/2021 | Weiss et al. |
| 10,973,871 | B2 | 4/2021 | Mitra et al. |
| 12,053,528 | B2 | 8/2024 | Weiss |
| 2002/0045601 | A1 | 4/2002 | Kawashima et al. |
| 2003/0176356 | A1 | 9/2003 | Yorio et al. |
| 2005/0042198 | A1 | 2/2005 | Smith et al. |
| 2006/0205639 | A1 | 9/2006 | Domb et al. |
| 2006/0217309 | A1 | 9/2006 | Naicker et al. |
| 2007/0015691 | A1 | 1/2007 | Chang et al. |
| 2007/0248645 | A1 | 10/2007 | Bague et al. |
| 2007/0249632 | A1 | 10/2007 | Zentner et al. |

(Continued)

FOREIGN PATENT DOCUMENTS

| | | | |
|---|---|---|---|
| EP | 2036538 | A1 | 3/2009 |
| EP | 2193795 | A1 | 6/2010 |

(Continued)

OTHER PUBLICATIONS

Morgan, Rhea V. et al; "Topical administration of cyclosporien for treatment of keartoconjuntivitis sicca in dogs." JAVMA (1991) 199(8) p. 1043-1046.*

(Continued)

*Primary Examiner* — Fred H Reynolds

(74) *Attorney, Agent, or Firm* — Medler Ferro Woodhouse & Mills PLLC

(57) ABSTRACT

Provided herein are formulations for topical ophthalmic formulations containing 0.087-0.093 wt % of cyclosporine, and methods of making and using such formulations. In some aspects and embodiments the formulations may include a polyoxyl lipid or fatty acid, and/or a polyalkoxylated alcohol and may include nanomicelles. Also included herein are methods of treating or preventing diseases or conditions, such as ocular diseases or conditions.

14 Claims, 1 Drawing Sheet

(56) References Cited

U.S. PATENT DOCUMENTS

2008/0299206 A1 12/2008 Lee et al.
2009/0074874 A1 3/2009 Amano et al.
2009/0092665 A1 4/2009 Mitra et al.
2009/0209599 A1 8/2009 Endo et al.
2009/0234004 A1 9/2009 Kabra et al.
2009/0286718 A1 11/2009 Stringer et al.
2009/0298956 A1 12/2009 Chowhan et al.
2011/0021443 A1 1/2011 Lambert et al.
2011/0040113 A1 2/2011 Wu et al.
2011/0152264 A1 6/2011 Reunamaki et al.
2011/0300195 A1 12/2011 Mitra et al.
2011/0311592 A1 12/2011 Birbara
2013/0023482 A1 1/2013 Gore et al.
2013/0045927 A1 2/2013 Dana et al.
2013/0065888 A1 3/2013 Cetina-Cizmek et al.
2013/0267591 A1 10/2013 Khopade et al.
2014/0057854 A1 2/2014 Mitra et al.
2015/0125494 A1 5/2015 Wang et al.
2015/0148299 A1 5/2015 Mitra et al.
2015/0157687 A1 6/2015 Mitra et al.
2015/0165048 A1 6/2015 Mitra et al.
2015/0352176 A1 12/2015 Takruri et al.
2015/0366953 A1 12/2015 Danias et al.
2016/0256520 A1 9/2016 Mitra et al.
2016/0256521 A1 9/2016 Mitra et al.
2017/0065611 A1 3/2017 Weiss
2018/0092927 A1 4/2018 Weiss et al.
2018/0133217 A1 5/2018 Weiss
2018/0333352 A1 11/2018 Weiss et al.
2019/0060397 A1 2/2019 Weiss et al.
2019/0231885 A1 8/2019 Weiss
2020/0237859 A1 7/2020 Takruri
2021/0268114 A1 9/2021 Weiss
2021/0338769 A1 11/2021 Mitra et al.
2024/0342086 A1 10/2024 Khopade et al.
2024/0358840 A1 10/2024 Weiss
2024/0423912 A1 12/2024 Khopade et al.
2025/0009837 A1* 1/2025 Hovanesian ......... A61K 9/0048

FOREIGN PATENT DOCUMENTS

EP 2478906 A1 7/2012
JP 2004-238346 A 8/2004
WO 2004/069181 A1 8/2004
WO 2004/096261 A1 11/2004
WO 2008/010341 A1 1/2008
WO 2008/137617 A1 11/2008
WO 2007/126110 A1 3/2009
WO 2009/048929 A1 4/2009
WO 2007/136134 A1 10/2009
WO 2013/167865 A1 11/2012
WO 2013/122801 A1 2/2013
WO 2014/032026 A1 2/2014
WO 2015/179527 A1 11/2015
WO 2016/178881 A1 11/2016
WO 2017/083167 A1 5/2017
WO 2017/083410 A1 5/2017
WO 2017/151657 A1 9/2017
WO 2017/152129 A1 9/2017
WO 2021/124301 A1 6/2021
WO 2021/224901 A2 11/2021
WO 2022/264006 A1 12/2022
WO 2023/021492 A1 2/2023
WO 2024/246776 A1 12/2024

OTHER PUBLICATIONS

Yu, Kimberly et al, "Systemic conditions associated with severity of dry eye signes and symptoms in the dry eye assessment and management study." Ophthalmal. (2021) 128 p. 1384-1392.*

Whitcher, John P. et al, "A simplified quantitative method for assessing deratoconjunctivitis sicca from the sjogren's syndrome international registry." Am. J. Ophthalmol. (2010) 149(3) p. 405-415.*

Izutsu, Ken-ichi; "Stabilization of therapetuic proteins by chemical and physical methods," in Therapeutic Proteins, Smales and James, ed. (2005) ISBN 1-58829-390-4, p. 287-292.*

The Oregon state college page on rotary evaporators, https://sites.science.oregonstate.edu/chemistry/courses/ch361-464/ch362/rotovap.htm, 2001.*

Goldberg et al., "A Phase 3, Randomized, Double-Masked Study of OTX-101 Ophthalmic Solution 0.09% in the Treatment of Dry Eye Disease," Ophthalmology 126(9): 1230-1237 (2019).

Horton et al., "Master the Maze of Artificial Tears," Review of Optometry (2018). Accessed at https://www.reviewofoptometry.com/article/master-the-maze-of-artificial-tears on Apr. 26, 2022.

Sheppard et al., "Efficacy and Safety of OTX-101, a Novel Nanomicellar Formulation of Cyclosporine A, for the Treatment of Keratoconjunctivitis Sicca: Pooled Analysis of a Phase 2b/3 and Phase 3 Study," Eye Contact Lens Suppl 1:S14-S19 (2020); Abstract.

Smyth-Medina et al., "Effect of OTX-101, a Novel Nanomicellar Formulation of Cyclosporine A, on Conjunctival Staining in Patients with Keratoconjunctivitis Sicca: A Pooled Analysis of Phase 2b/3 and 3 Clinical Trials," J Ocul Pharamcol Ther 35(7): 388-94 (2019).

Restriction Requirement in U.S. Appl. No. 17/200,454, dated Mar. 16, 2023.

Non-final Office Action in U.S. Appl. No. 17/200,454, dated Jun. 8, 2023.

Final Office Action in U.S. Appl. No. 17/200,454, dated Sep. 27, 2023.

Roberts et al., "Comparison of topical cyclosporine, punctal occlusion, and a combination for the treatment of dry eye," Cornea 26(7):805-809 (2007).

Acheampong et al., "Distribution of cyclosporin A in ocular tissues after topical administration to albino rabbits and beagle dogs," Current Eye Research, 18(2):91-103 (1999).

Aragona et al., "Sodium hyaluronate eye drops of different osmolarity for the treatment of dry eye in Sjogren's syndrome patients," Br J Ophthamol 86:879-884 (2002).

Auven Therapeutics: "Auven Therapeutics Announces Positive Results From Pivotal Clinical Trial of Seciera (OTX-101) in Dry Eye Disease," Nov. 13, 2015, XP55632570, retrieved from the Internet on Mar. 26, 2021: https://www.globalnewswire.com/news-release/2015/11/13/787027/10156193/en/Auven-Therapeutics-Announces-Positive-Results-From-Pivotal-Clinical-Trial-of-Seciera-OTX-101-in-Dry-Eye-Disease.html.

Berge et al., "Pharmaceutical Salts," Journal of Pharmaceutical Science 66(1):1-19 (1977).

Binks et al., "Stability of oil in water emulsions in a low interfacial tension system," Langmuir 16:1025-1034 (2000).

Cholkar et al., "Topical, Aqueous, Clear Cyclosporine Formulation Design for Anterior and Posterior Ocular Delivery," Translational Vision Science & Technology 4(3):1 (2015).

The Cold Spring Harbor protocol for phosphate buffer, https://cshprotocols.cshlp.org/content/2006/1/pdb.rec8303, available online Oct. 2012.

"Cremophor RH40," Technical Information, Oct. 2010, BASF.

De Aguiar et al., "The interfacial tension of nanoscopic oil droplets in water is hardly affected by SDS surfactant," J. Am. Chem. Sox. 132:2122-2123 (2010).

Deckner, G., "Tests for predicting emulsion/suspension stability," Prospector (Oct. 25, 2013).

Donnenfield et al., "Topical Ophthalmic Cyclosporine: Pharmacology and Clinical Uses," Survey of Ophthalmology 54(3):321-338 (2009).

"Duo Trav 40," Product Summary Annexes I, II, & III, first published on Feb. 12, 2009, European Medicines Agency. Accessible at https://www.ema.europa.eu/documents/product-information/duotrav-epar-product-information_en.pdf.

Farkas et al., "Dynamic light scattering distributions by any means," J. Nanopart. Res. 23:120 (2021).

Guo et al., "Nanomicelle formulation for topical delivery of cyclosporine A into the cornea: in vitro mechanism and in vivo permeation evaluation," Scientific Reports 5:12968 (2015).

(56) References Cited

OTHER PUBLICATIONS

Gupta et al., "Kinetics of the change in droplet size during nanoemulsion formation," Langmuir 32:11551-11559 (2016).
Hackett et al., "Ophthalmic Toxicology and Assessing Ocular Irritation," Dermatoxicology, 5th Edition, Ed. F. N. Marzulli and H.I. Maibach. Washington, D.C.: Hemisphere Publishing Corporation. 1996: 299-305 and 557-566.
Howell et al., "Combinatorial targeting of early pathways profoundly inhibits neurodegeneration in a mouse model of glaucoma," Neurobiology of Disease 71:44-52 (2014).
Hoyng et al., "Iloprost, a stable prostacyclin analog, reduces intraocular pressure," Investigative Ophthamology & Visual Science 28(3):470-476 (1987).
Izutsu, K., "Stabilization of therapeutic proteins by chemical and physical methods," Therapeutic Proteins, Smales & James, Ed (2005), ISBN 1-58829-390-4.
Kymionis et al., "Treatment of chronic dry eye: focus on cyclosporine," Clin Ophthalmol. 2(4):829-836 (2008).
Leong et al., "Minimizing oil droplet size using ultrasonic emulsification," Ultrason. Sonochem. 16:721-727 (2009).
Li et al., "Resolvin E1 Improves Tear Production and Decreases Inflammation in a Dry Eye Mouse Model," Journal of Ocular Pharmacology and Therapeutics 26(5):431-439 (2010).
"Lipids," IUPAC Compendium of Chemical Terminology (Gold Book), downloaded Jun. 2, 2017 from http://goldbook.iupac.org/src_PAC_1995671307.html.
Mohajeri et al., "Effect of temperature on the critical micelle concentration and micellization thermodynamics of nonionic surfactants: polyoxyethylene sorbitan fatty acid esters," E-J Chem 9(4):2268-2274 (2012).
Perez-Santonja et al., "Inhibition of Corneal Neovascularization by Topical Bevacizumab (Anti-VEGF) and Sunitinib (Anti-VEGF and Anti-PDGF) in an Animal Model," American Journal of Ophthalmology 150:519-528 (2010).
Quintana-Hau et al., "Characterization of the Novel Ophthalmic Drug Carrier Sophisen in Two of Its Derivatives: 3A Ofteno™ and Modisuk-A Ofteno™," Drug Development and Industrial Pharmacy 31:263-269 (2005).
Resch et al., "Effect of Dual Endothelin Receptor Blockade on Ocular Blood Flow in Patients with Glaucoma and Healthy Subjects," Invest Ophthalmol Vis Sci 50(1):358-363 (2009).
Restasis Prescribing Information, Allergan, Inc., downloaded Mar. 23, 2014.
Schmidts et al., "Influence of hydrophilic surfactants on the properties of multiple W/O/W emulsions," Journal of Colloidal Interface Science 33 8:184-192 (2009).
Settimio et al., "Resolvin D1 Reduces the immunoinflammatory Response of the Rat Eye following Uveitis," Mediators of Inflammation vol. 2012, Article ID 318621 (2012).
Tauber et al., "A Phase II/III, randomized, double-masked, vehicle-controlled, dose-ranging study of the safety and efficacy of OTX-101 in the treatment of dry eye disease," Clin Ophthamol 12:1921-1929 (2018).
Tostado et al., "Experimental study on dynamic interfacial tension with mixtures of sds-peg as surfactants in a coflowing microfluidic device," Langmuir 28:3120-3128 (2012).
"Travatan," Drug Label Information, updated Jul. 20, 2011 on Daily Med, USNLM. Accessible at https://dailymed.nlm.nih.gov/dailymed/drugInfo.cfi:n?setid=db08d5f3-6713-4372-a66c-fad3018ef5c6.
Troiano et al., "Effect of Hypotonic 0.4% Hyaluronic Acid Drops in Dry Eye Patients: A Cross-Over Study," Cornea 27(10):1126-1130 (2008).
Varade et al., "Effect of salt on the micelles of cetyl pyridinium chloride," Coll. Surf. A: Physiochem. Eng. Aspects 259:95-101 (2005).
"Vitamin E," Medline Plus, downloaded Jun. 2, 2017 from https://medlineplus.gov/ency/article/002406.htm.
International Search Report issued in PCT/US2013/056513, dated Nov. 18, 2013.
International Search Report issued in PCT/US2015/031788, dated Aug. 26, 2015.
International Search Report issued in PCT/US2016/029602, dated Jul. 15, 2016.
International Search Report issued in PCT/US2016/061167, dated Dec. 27, 2016.
International Search Report issued in PCT/US2016/060391, dated Jan. 10, 2017.
International Search Report issued in PCT/US2017/020008, dated May 23, 2017.
International Search Report issued in PCT/US2017/020795, dated Jun. 16, 2017.
Non-Final Office Action issued in U.S. Appl. No. 13/975,175, dated Dec. 19, 2013.
Final Office Action issued in U.S. Appl. No. 13/975,175, dated Apr. 1, 2014.
Non-Final Office Action issued in U.S. Appl. No. 13/975,175, dated Jul. 22, 2014.
Non-Final Office Action issued in U.S. Appl. No. 14/611,993, dated Nov. 10, 2015.
Non-Final Office Action issued in U.S. Appl. No. 14/611,993, dated Nov. 18, 2015.
Non-Final Office Action issued in U.S. Appl. No. 14/629,883, dated Nov. 13, 2015.
Non-Final Office Action issued in U.S. Appl. No. 15/153,510, dated Jan. 23, 2017.
Final Office Action issued in U.S. Appl. No. 15/153,510, dated Jun. 9, 2017.
Non-final Office Action issued in U.S. Appl. No. 15/153,640, dated Jan. 23, 2017.
Non-Final Office Action issued in U.S. Appl. No. 15/163,640, dated Dec. 11, 2017.
Final Office Action issued in U.S. Appl. No. 15/153,640, dated Jun. 12, 2017.
Final Office Action issued in U.S. Appl. No. 15/153,640, dated May 31, 2018.
Final Office Action issued in U.S. Appl. No. 15/153,640, dated Nov. 26, 2018.
Non-Final Office Action issued in U.S. Appl. No. 15/354,568, dated Jun. 6, 2017.
Non-Final Office Action issued in U.S. Appl. No. 15/571,482, dated Aug. 3, 2018.
Final Office Action issued in U.S. Appl. No. 15/571,482, dated Dec. 18, 2018.
Non-Final Office Action issued in U.S. Appl. No. 15/833,699, dated May 29, 2018.
Non-Final Office Action issued in U.S. Appl. No. 15/772,779, dated May 15, 2020.
Final Office Action issued in U.S. Appl. No. 15/772,779, dated Dec. 15, 2020.
International Search Report issued in PCT/IB2022/055462, dated Sep. 8, 2022.
ClinicalTrials.gov ID: NCT04342988, "Effect of Cequa Treatment on Accuracy of Pre-operative Biometry & Higher Order Aberrations in Dry Eye Patients Undergoing Cataract Surgery," Mar. 12, 2021. Accessed at <www.clinicaltrials.gov/ct2/show/NCT04342988>.
Donnenfeld et al., "Cyclosporine 0.05% to improve visual outcomes after multi focal intraocular lens implantation," J Cataract Refract Surg 36(7): 1095-1100 (2010).
Ganesh et al., "Topical Cyclosporine (0.05%) for Management of Dry Eyes in Patients Undergoing Cataract Surgery—A Comparative Study," The Open Ophthalmology Journal 13(1):34-42 (2019).
Addisu et al., "Patients' Preoperative Expectation and Outcome of Cataract Surgery at Jimma University Specialized Hospital-Department of Ophthalmology," Ethiop J Health Sci. 21(1): 47-55 (2011).
Epitropoulos et al., "Effect of tear osmolarity on repeatability of keratometry for cataract surgery planning," J Cataract Refract Surg 41(8): 1672-1677 (2015).
Gollogly et al., "Increasing incidence of cataract surgery: population-based study," J Cataract Refract Surg. 39(9): 1383-1389 (2013).

(56) References Cited

OTHER PUBLICATIONS

Hovanesian et al., "The Effect of Lifitegrast on Refractive Accuracy and Symptoms in Dry Eye Patients Undergoing Cataract Surgery," Clin Ophthamol 14: 2709-2716 (2020).
Jeong et al., "The effect of ocular biometric factors on the accuracy of various IOL power calculation formulas," BMC Ophthalmol 17: 62 (2017).
Lee et al., "Biometry and intraocular lens power calculation," Curr Opin Ophthalmol 19(1): 13-17 (2008).
Li et al, "Investigation of Dry Eye Disease and Analysis of the Pathogenic Factors in Patients after Cataract Surgery," Cornea 26: S16-S20 (2007).
Mönestam, E., "Long-term outcomes of cataract surgery: 15-year results of a prospective study," J Cataract Refract Surg. 42(1): 19-26 (2016).
Norrby, S., "Sources of error in intraocular lens power calculation," J Cataract Refract Surg 34(3): 368-376 (2008).
Sahin et al., "Clinically relevant biometry," Curr Opin Ophthamol 23(1): 47-53 (2012).
Sheard, R., "Optimising biometry for best outcomes in cataract surgery," Eye 28(2): 118-125 (2014).
International Search Report issued in PCT/IB2021/059176, dated Nov. 29, 2021.
Chazotte, "Labeling Golgi with Fluorescent Ceramides," Cold Spring Harbor Protocols 2012(8): pdb.prot070599 (2012).
International Search Report issued in PCT/IB2022/057851, dated Jan. 2, 2023.
Lalu et al., "Novel nanosystems for the treatment of ocular inflammation: Current paradigms and future research directions," J Control Release 268: 19-39 (2017).
Mandal et al., "Ocular Pharmacokinetics of a Topical Ophthalmic Nanomicellar Solution of Cyclosporine (Cequa ) for Dry Eye Disease", Pharma Res 36: 36 (2019).
International Search Report issued in PCT/IB2024/055222, dated Sep. 23, 2024.
Non-Final Office Action issued in U.S. Appl. No. 15/153,640, dated Jul. 5, 2019.
Restriction Requirement issued in U.S. Appl. No. 17/200,454, dated Mar. 16, 2023.
Non-Final Office Action issued in U.S. Appl. No. 17/200,454, dated Jun. 8, 2023.
Final Office Action issued in U.S. Appl. No. 17/200,454, dated Sep. 27, 2023.
Notice of Allowance issued in U.S. Appl. No. 17/200,454, dated Mar. 28, 2024.
Begley et al., "Review and analysis of grading scales for ocular surface staining," *The Ocular Surface* 17:208-220 (2019).
Lemp et al., "Report of the National Eye Institute/Industry Workshop on Clinical Trials in Dry Eyes," *The CLAO Journal* 21(4):221-232 (1995).
Schaumberg et al., "Development and Validation of a Short Global Dry Eye Symptom Index," *The Ocular Surface* 5:50-57 (2007).
Schechter et al., "Effect of OTX-101 in Patients with Dry Eye Disease at Day 14 of Treatment: Ocular Surface Endpoint Results from the Phase 2b/3 Clinical Trial," *Clinical Ophthalmology* 16:4145-4151 (2022).
Cequa, FDA Full Prescribing Information, available at https://www.accessdata.fda.gov/drugsatfda_docs/label2018/210913s000lbl.pdf. Published 2018.
Ozalp et al., "Assessment of Phosphate and Osmolarity Levels in Chronically Administered Eye Drops," Turk J Ophthalmol 49(3):123-129 (2019).
Non-Final Office Action issued in U.S. Appl. No. 18/683,943, dated Jan. 7, 2026.
Final Office Action issued in U.S. Appl. No. 18/683,943, dated May 6, 2026.
Non-Final Office Action issued in U.S. Appl. No. 18/683,932, dated May 6, 2026.

* cited by examiner

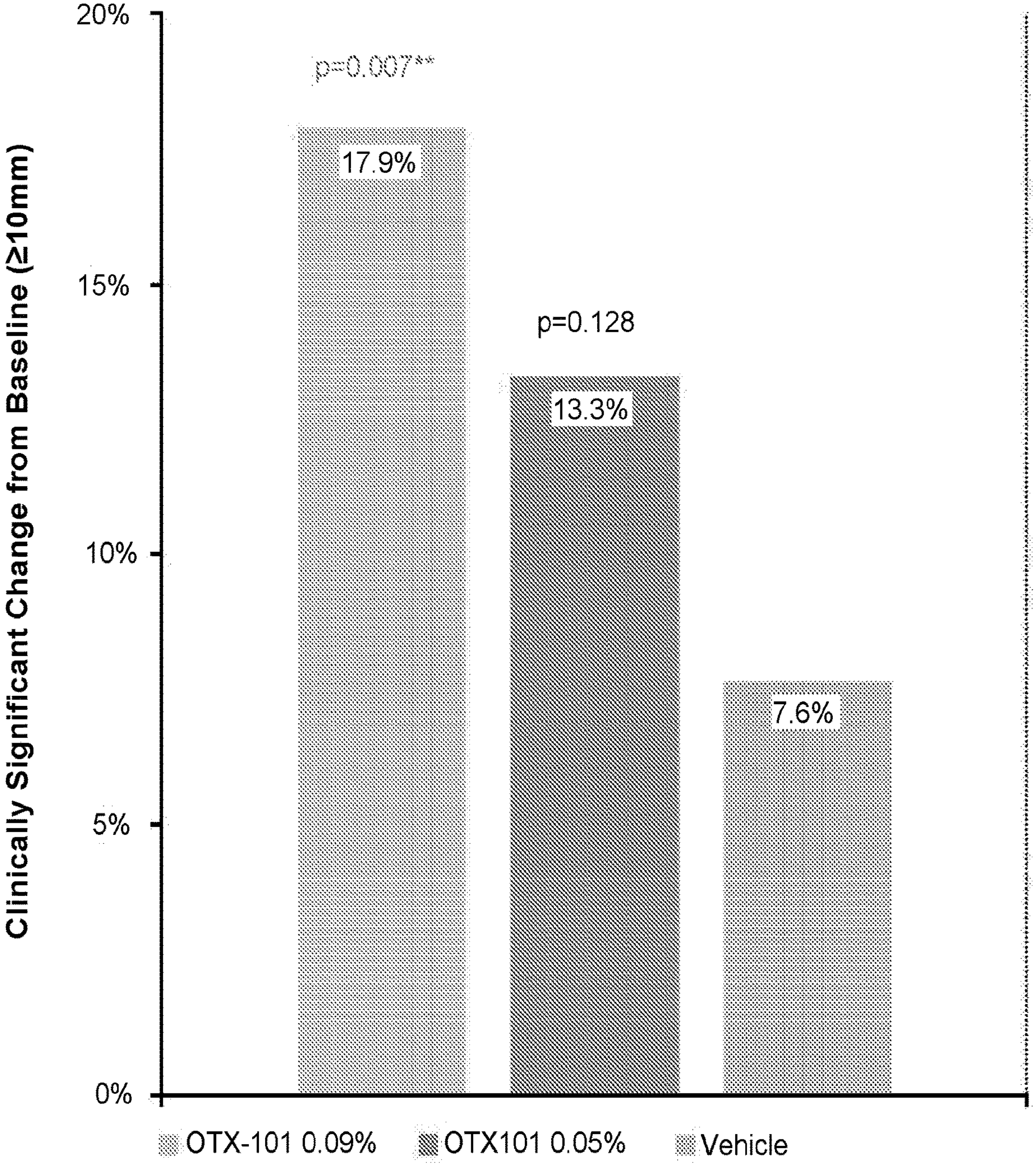
20%
15%
10%
5%
0%
Clinically Significant Change from Baseline (≥10mm)
p=0.007**
17.9%
p=0.128
13.3%
7.6%
OTX-101 0.09%
OTX101 0.05%
Vehicle

TOPICAL CYCLOSPORINE-CONTAINING FORMULATIONS AND USES THEREOF

FIELD OF THE INVENTION

The present disclosure relates to the field of cyclosporine-containing formulations for topical administration thereof, such as ophthalmic formulations containing 0.087-0.093% of cyclosporine, and methods of making and using such formulations.

BACKGROUND OF THE INVENTION

The information provided herein and references cited are provided solely to assist the understanding of the reader, and does not constitute an admission that any of the references or information is prior art to the present invention.

United States Patent Application Nos US2010/0310462 and US2009/0092665 disclose drug delivery systems for ophthalmic use that have nanomicelles that include vitamin E TPGS.

Travoprost is an opthalmic solution formulation for reduction of elevated intraocular pressure in patients with glaucoma or ocular hypertension. It contains 0.5% HCO-40, 0.004% prostaglandin analog travoprost as active ingredient and propylene glycol as organic solvent. (nlm.nih.gov/dailymed/lookup.cfm?setid=338e7ff4-Od91-4208-a45d-bfa2be52334d on the world-wide web). However, this composition is not in the form of nanomicelles. (ema.europa.eu/docs/en_GB/document_library/EPAR_-_Product_Information/human/000665/WC500038389.pelf on the world-wide web).

U.S. Pat. No. 8,980,839 discloses an aqueous ophthalmic solution, said solution comprising cyclosporine, a polyoxyl lipid or fatty acid and a polyalkoxylated alcohol. The patent contemplates HCO-40 as polyoxyl lipid and Octoxynol-40 as the polyalkoxylated alcohol.

The most common adverse effect following the use of RESTATIS® (cyclosporine 0.05% ophthalmic emulsion) is ocular burning in patients as reported in 17% cases. Other adverse reactions include conjunctiva! hyperemia, epiphora, eye pain, discharge, foreign body sensation, pruritis, stinging and visual disturbance (in 1-5% patients).

SUMMARY OF THE INVENTION

The present disclosure relates to ophthalmic topical formulations comprising 0.087-0.093 wt % cyclosporine. In certain aspects and embodiments, formulations comprising 0.087-0.093 wt % cyclosporine as described herein do not produce the side effects such as reduced visual acuity, blurred vision, increased lacrimation, eye discharge and dysgeusia as reported in other ophthalmic formulations such as Xiidra® (lifitegrast ophthalmic solution), thus providing a better safety profile.

The formulations of the instant disclosure are based, at least in part, on the surprising and unexpected findings that formulations comprising 0.087-0.093 wt % cyclosporine can have a higher effectiveness and can be unexpectedly stable, for example, in large scale manufacturing. Features and advantages of formulations of the instant disclosure that could not have been predicted prior to the present disclosure include the improved handling thereof upon preparation at industrial scale, i.e., various aspects and embodiments of formulations of the instant disclosure remain fully fluid in the carrier therefore, and resist the propensity to precipitate upon handling thereof.

The formulations of the present disclosure in certain embodiments are surprisingly stable at high temperatures, for example, temperatures above about 40 degrees C.

In certain aspects and embodiments, the formulations of the present disclosure further include a polyoxyl lipid or fatty acid, and/or a polyalkoxylated alcohol and may include nanomicelles.

Nanomicelles contemplated by the present disclosure typically have a particle size in the range of about 1-100 nm; in some embodiments, the particle size falls in the range of about 5-50 nm; in some embodiments, the particle size falls in the range of about 10-40 nm; in some embodiments, the particle size is about 15 nm.

In one aspect, the topical ophthalmic formulations of the present disclosure comprise 0.087-0.093 wt % cyclosporine and one or more additional formulation ingredients.

In one of the embodiments of the above aspect, formulations contemplated herein are stable at temperatures above 40 degrees C.

In another embodiment of the above aspect, the formulation of the present disclosure is a clear aqueous solution.

In another embodiment of the above aspect, the formulation of the present disclosure is substantially free of organic solvents.

In another embodiment of the above aspect, the formulation of the present disclosure is free of preservatives.

In another embodiment of the above aspect, the formulation of the present disclosure comprises one or more additional formulation ingredients.

In another embodiment of the above aspect, the formulation of the present disclosure are mixed nanomicellar formulations.

In another embodiment of the above aspect, the formulation of the present disclosure comprise cyclosporine encapsulated in core of mixed nanomicelles.

In another embodiment of the above aspect, the nanomicelles have a particle size of about 5-100 nm In another embodiment of the above aspect, the formulation of the present disclosure comprises one or more additional ingredients.

In another embodiment of the above aspect, the additional ingredients are selected from the group consisting of a polyoxyl lipid or a fatty acid and a polyalkoxylated alcohol.

In another embodiment of the above aspect, the polyoxyl lipid is a polyoxyl castor oil.

In another embodiment of the above aspect, the polyoxyl lipid is selected from the group consisting of HCO-40, HCO-60, HCO-80 and HCO-100.

In another embodiment of the above aspect, the polyoxyl lipid or fatty acid is present in an amount of about 0.1-5 wt % of the formulation.

In another embodiment of the above aspect, the polyalkoxylated alcohol is octoxynol 40.

In another embodiment of the above aspect, polyalkoxylated alcohol is present in an amount of about 0.002-4 wt % of the formulation.

In another embodiment of the above aspect, the formulations of the present disclosure comprising additional formulation ingredients are further selected from the group consisting of additives, adjuvants, buffers, tonicity agents, bioadhesive polymers and preservatives.

In another embodiment of the above aspect, buffer is selected from the group consisting of phosphate, borate, acetate, citrate, carbonate and borate-polyol complexes.

In another embodiment of the above aspect, tonicity agent is selected from the group consisting of mannitol, sodium chloride, sodium nitrate, sodium sulfate, dextrose, xylitol or combinations thereof.

In another embodiment of the above aspect, bioadhesive polymer is selected from the group consisting of carbopol, carbophils, cellulose derivatives, gums such as xanthum, karaya, guar, tragacanth, agarose and other polymers such as povidone, polyethylene glycol, poloxamers, hyaluronic acid or combinations thereof.

In another embodiment of the above aspect, the bioadhesive polymer is povidone.

In certain aspects and embodiments, the formulations of the present disclosure comprise further active agents.

In an embodiment of the above aspect, further active ingredients are selected from the group consisting of resolvin, resolvin-like compounds, steroids, antibiotics, antivirals, hormones, cytokines, toxins, vitamins or combinations thereof.

In certain aspects and embodiments, the formulations of the present disclosure comprise 0.087-0.093 wt % cyclosporine, wherein the said formulation demonstrates a clinically significant improvement as compared to the vehicle in tear production with ≥10 mm increase in Schimer test score from baseline.

In an embodiment of the above aspect, the formulations of the present disclosure demonstrate an early onset as compared to other formulations of cyclosporine A.

In certain aspects and embodiments, the formulations of the present disclosure comprise:

0.087-0.093 wt % cyclosporine, about 0.1-6 wt % hydrogenated 40 polyoxyl castor oil, and about 0.002-4 wt % octoxynol-40.

In certain aspects and embodiments, the formulations of the present disclosure comprise:

0.087-0.093 wt % cyclosporine, about 1.0 wt % hydrogenated 40 polyoxyl castor oil, and about 0.05 wt % octoxynol-40 (Igepal).

In certain aspects and embodiments, the formulations of the present disclosure further comprise:

about 0.20-0.405 wt % sodium phosphate monobasic, about 0.23-0.465 wt % sodium phosphate dibasic, about 0.05 wt % sodium chloride, about 0.3 wt % povidone K90, sodium hydroxide/hydrochloric acid and water for injection.

As used herein in connection with numerical values, the terms "approximately" and "about" mean+/−10% of the indicated value, including the indicated value.

In some aspects, formulations contemplated herein comprise 0.088-0.093 wt % cyclosporine.

In some aspects, formulations contemplated herein comprise 0.089-0.093 wt % cyclosporine. In some embodiments of such aspects, the formulations of the present disclosure comprise:

0.089-0.093 wt % cyclosporine, about 1.0 wt % hydrogenated 40 polyoxyl castor oil, and about 0.05 wt % octoxynol-40 (Igepal).

In certain aspects and embodiments, the formulations of the present disclosure further comprise:

about 0.20 wt % sodium phosphate monobasic, about 0.23 wt % sodium phosphate dibasic, about 0.05 wt % sodium chloride, about 0.3 wt % povidone K90, sodium hydroxide/hydrochloric acid and water for injection.

In some embodiments of such aspects, the formulations of the present disclosure comprise:

0.09-0.093 wt % cyclosporine, about 1.0 wt % hydrogenated 40 polyoxyl castor oil, and about 0.05 wt % octoxynol-40 (Igepal).

In certain aspects and embodiments, the formulations of the present disclosure further comprise:

about 0.405 wt % sodium phosphate monobasic, about 0.465 wt % sodium phosphate dibasic, about 0.05 wt % sodium chloride, about 0.3 wt % povidone K90, sodium hydroxide/hydrochloric acid and water for injection.

In some aspects, formulations contemplated herein comprise 0.091-0.093 wt % cyclosporine.

In some aspects, formulations contemplated herein comprise 0.092-0.093 wt % cyclosporine.

In some aspects, formulations contemplated herein comprise 0.087-0.092 wt % cyclosporine.

In some aspects, formulations contemplated herein comprise 0.087-0.091 wt % cyclosporine.

In some aspects, formulations contemplated herein comprise 0.087-0.09 wt % cyclosporine. In some embodiments of such aspects, the formulations of the present disclosure comprise:

0.087-0.09 wt % cyclosporine, about 1.0 wt % hydrogenated 40 polyoxyl castor oil, and about 0.05 wt % octoxynol-40 (Igepal).

In certain aspects and embodiments, the formulations of the present disclosure further comprise:

about 0.20 wt % sodium phosphate monobasic, about 0.23 wt % sodium phosphate dibasic, about 0.05 wt % sodium chloride, about 0.3 wt % povidone K90, sodium hydroxide/hydrochloric acid and water for injection.

In some embodiments of such aspects, the formulations of the present disclosure comprise:

0.087-0.089 wt % cyclosporine, about 1.0 wt % hydrogenated 40 polyoxyl castor oil, and about 0.05 wt % octoxynol-40 (Igepal).

In certain aspects and embodiments, the formulations of the present disclosure further comprise:

about 0.405 wt % sodium phosphate monobasic, about 0.465 wt % sodium phosphate dibasic, about 0.05 wt % sodium chloride, about 0.3 wt % povidone K90, sodium hydroxide/hydrochloric acid and water for injection.

In some aspects, formulations contemplated herein comprise 0.087 wt % cyclosporine.

In some aspects, formulations contemplated herein comprise 0.088 wt % cyclosporine.

In some aspects, formulations contemplated herein comprise 0.089 wt % cyclosporine.

In some aspects, formulations contemplated herein comprise 0.09 wt % cyclosporine.

In some aspects, formulations contemplated herein comprise 0.091 wt % cyclosporine.

In some aspects, formulations contemplated herein comprise 0.092 wt % cyclosporine.

In some aspects, formulations contemplated herein comprise 0.093 wt % cyclosporine.

In certain aspects and embodiments, formulations as described herein are particularly suitable for anterior eye delivery, or posterior eye delivery, or anterior and posterior eye delivery.

In certain aspects and embodiments, the formulations of the present disclosure consist essentially of:

0.087-0.093 wt % cyclosporine,
about 1.0 wt % hydrogenated 40 polyoxyl castor oil, and
about 0.05 wt % octoxynol-40 (Igepal), and
optionally further consist essentially of:
about 0.20-0.405 wt % sodium phosphate monobasic,
about 0.23-0.465 wt % sodium phosphate dibasic,
about 0.05 wt % sodium chloride,
about 0.3 wt % povidone K90,
NaOH/HCl, and
water for injection.

In some embodiments the formulation has nanomicelles with a relatively increased entrapment efficiency; in such embodiments the cyclosporine may be at least about 0.087%, or at least about 0.088%, or at least about 0.089%, or at least about 0.09%, or at least about 0.091%; or at least about 0.092%; or at least about 0.093%; or no greater than 0.087%; or between 0.087 and 0.093%; or between 0.088 and 0.093%; or between 0.089 and 0.093%, or between 0.09 and 0.093%; or about 0.087%, or about 0.088%, or about 0.089%; or about 0.09%; or about 0.091%; or about 0.092%; or about 0.093%; of the formulation and is present in nanomicelles of the formulation.

Accordingly, in one aspect provided is an ophthalmic formulation that includes 0.087-0.093 wt % cyclosporine, a polyoxyl lipid or fatty acid and a polyalkoxylated alcohol. In some embodiments the formulations include nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 5%; or 0.6 and 5%; or 0.7 and 5%; or 0.8 and 5%; or 0.9 and 5%; or 1 and 5%; or 1 and 4%; or 1 and 3%; or 1 and 2%; or about 1%; or greater than 0.5%; or greater than 0.6%, or greater than 0.7%; or greater than 0.8%; or greater than 0.9%; or greater than 1% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation includes a polyalkoxylated alcohol that is octoxynol-40. In some embodiments, the formulation includes a polyalkoxylated alcohol (such as octoxynol-40) present between 0.01 and 1%; or between 0.02 and 1%; or 0.03 and 1%; or 0.04 and 1%; or 0.05 and 1%; or 0.06 and 1%; or 0.07 and 1%; or 0.08 and 1%; or about 1% by weight of the formulation.

As used herein, the term "polyoxyl lipid or fatty acid" refers to mono- and diesters of lipids or fatty acids and polyoxyethylene diols. Polyoxyl lipids or fatty acids may be numbered ("n") according to the average polymer length of the oxyethylene units (e.g., 40, 60, 80, 100) as is well understood in the art. The term "n:?. 40 polyoxyl lipid" means that the ployoxyl lipid or fatty acid has an average oxyethylene polymer length equal to or greater than 40 units. Stearate hydrogenated castor oil and castor oil are common lipids/fatty acids commercially available as polyoxyl lipids or fatty acid, however, it is understood that any lipid or fatty acid could polyoxylated to become a polyoxyl lipid or fatty acid as contemplated herein. Examples of polyoxyl lipid or fatty acids include without limitation HCO-40, HCO-60, HCO-80, HCO-100, polyoxyl 40 stearate, polyoxyl 35 castor oil.

In some embodiments of any of the compositions and methods described herein, the average polymer length of the oxyethylene units of a polyoxyl lipid or fatty acid is longer for a relatively larger active ingredient and is shorter for a relatively smaller active ingredient; for example in some embodiments in which the active ingredient is a resolvin or resolvin-like compound the polyoxyl lipid is HCO-60 and in some embodiments where the active ingredient is cyclosporine A (which is larger than a resolvin) the polyoxyl lipid is HCO-80 or HCO-100.

As used herein, the term "micelle" or "nanomicelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle. The in some embodiments, ophthalmic compositions of the present disclosure include an aqueous, clear, mixed micellar solution.

In another aspect, provided is an ophthalmic formulation, comprising 0.087-0.093 wt % cyclosporine, and a n≥40 polyoxyl lipid or fatty acid. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.1 and 2%, or 0.2 and 2%, or 0.3 and 2%; or 0.4 and 2%; or 0.5 and 2%; or 0.6 and 2%; or 0.7 and 2%; or 0.8 and 2%; or 0.9 and 2%; or 1 and 2%; or 0.1 and 6%; or about 4%; or greater than 0.4%; or greater than 1%, or greater than 1.5%; or greater than 2%; or greater than 3%; or greater than 4% by weight of the formulation. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In another aspect, provided is an ophthalmic formulation, that includes 0.087-0.093 wt % cyclosporine and a polyoxyl lipid or fatty acid; wherein said polyoxyl lipid or fatty acid is present in an amount equal to or greater than 1% of said formulation. In a similar aspect, provided is an ophthalmic formulation, that includes 0.087-0.093 wt % cyclosporine and a polyoxyl lipid or fatty acid; wherein said polyoxyl lipid or fatty acid is present in an amount equal to or greater than 0.05% of said formulation. In some embodiments the formulations includes nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO- 100. In some embodiments the polyoxyl lipid or fatty acid (such as a polyoxyl castor oil such as HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In another aspect, provided is an ophthalmic formulation, that includes 0.087-0.093 wt % cyclosporine and a polyoxyl lipid or fatty acid; wherein said formulation comprises nanomicelles. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-40, HCO-60, HCO-80 or HCO-100) is present between 0.5 and 2%, or 0.7 and 2%, or between 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100. In some embodiments, the formulation further includes polyalkoxylated alcohol. In some embodiments, the formulation further includes polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In a further aspect provided is an ophthalmic formulation, comprising 0.087-0.093 wt % cyclosporine, 1-5% of one or more selected from the group consisting of HCO-40, HCO-60, HCO-80 and HCO-100; and about 0.01-0.05% octoxynol-40.

In another aspect, provided is ophthalmic formulation, comprising 0.087-0.093 wt % cyclosporine, 1-5% of one or more selected from the group consisting of HCO-40, HCO-60, HCO-80 and HCO-100; and about 0.01-0.05% octoxynol-40.

In yet another aspect, provided is an ophthalmic formulation, comprising 0.087-0.093 wt % cyclosporine, 1-5% of one or more selected from the group consisting of HCO-40, HCO-60, HCO-80 and HCO-100; and about 0.01-0.05% octoxynol-40.

In another aspect, provided is an ophthalmic formulation, comprising 0.087-0.093 wt % cyclosporine, 1-5% of one or more selected from the group consisting of HCO-40, HCO-60, HCO-80 and HCO-100; and about 0.01-0.05% octoxynol-40.

In a further aspect provided is an ophthalmic formulation, comprising 0.087-0.093 wt % cyclosporine, about 4% of HCO-60 and about 0.01-0.05% octoxynol-40.

In another aspect provided is an ophthalmic formulation, comprising 0.087-0.093 wt % cyclosporine, 0.7-1.5% of one or more selected from the group consisting of HCO-40, HCO-60, HCO-80 and HCO-100; and about 0.05-0.1% octoxynol-40.

In another aspect, provided is ophthalmic formulation, comprising 0.087-0.093 wt % cyclosporine, 0.7-1.5% of one or more selected from the group consisting of HCO-40, HCO-60, HCO-80 and HCO-100; and about 0.05-0.1% octoxynol-40.

In yet another aspect, provided is an ophthalmic formulation, comprising 0.087-0.093 wt % cyclosporine, 0.7-1.5% of one or more selected from the group consisting of HCO-40, HCO-60, HCO-80 and HCO-100; and about 0.05-0.1% octoxynol-40.

In another aspect, provided is an ophthalmic formulation, comprising 0.087-0.093 wt % cyclosporine, 0.7-1.5% of one or more selected from the group consisting of HCO-40, HCO-60, HCO-80 and HCO-100; and about 0.05-0.1% octoxynol-40.

In a further aspect provided is an ophthalmic formulation, comprising 0.087-0.093 wt % cyclosporine, about 1% of HCO-60 and about 0.05-0.1% octoxynol-40.

In various embodiments of any of the aspects and embodiments described herein, the formulation includes nanomicelles.

In some embodiments of the aspects and embodiments described herein, the formulation includes a polyoxyl lipid or fatty acid. In some embodiments the polyoxyl lipid or fatty acid is a polyoxyl castor oil. In some embodiments, the polyoxyl lipid or fatty acid is one or more selected from HCO-40, HCO-60, HCO-80 or HCO-100. In some embodiments the polyoxyl lipid or fatty acid (such as a polyoxyl castor oil such as HCO-60, HCO-80 or HCO-100) is present between 0.5 and 2%, or 0.7 and 2%, or 1 and 6%; or 2 and 6%; or 2 and 6%; or 3 and 6%; or 4 and 6%; or 2 and 5%; or 3 and 5%; or 3 and 5%; or 2 and 6%; or about 4%; or greater than 0.7%; or greater than 1%, or greater than 1.5%; or greater than 2%; or greater than 3%; or greater than 4% by weight of the formulation. In some embodiments the polyoxyl lipid is HCO-40. In some embodiments the polyoxyl lipid is HCO-60. In some embodiments the polyoxyl lipid is HCO-80. In some embodiments the polyoxyl lipid is HCO-100.

In some embodiments of the aspects and embodiments disclosed herein, includes a polyalkoxylated alcohol. In some embodiments, the formulation includes a polyalkoxylated alcohol that is octoxynol-40. In some embodiments, the formulation includes a polyalkoxylated alcohol (such as octoxynol-40) present between 0.002 and 4%; or between 0.005 and 3%; or between 0.005 and 2%; or between 0.005 and 1%; or between 0.005 and 0.5%; or between 0.005 and 0.1%; or between 0.005 and 0.05%; or between 0.008 and 0.02%; or between 0.01 and 0.1%; or between 0.02 and 0.08%; or between 0.005 and 0.08%; or about 0.05%, or about 0.01% by weight of the formulation.

In certain aspects and embodiments, the present disclosure contemplates stable emulsions comprising:

0.087-0.093 wt % cyclosporine,
about 1.0 wt % hydrogenated 40 polyoxyl castor oil, and
about 0.05 wt % octoxynol-40 (Igepal), and
optionally further comprising:
0.20-0.405 wt % sodium phosphate monobasic,
0.23-0.465 wt % sodium phosphate dibasic,
about 0.05 wt % sodium chloride,
about 0.3 wt % povidone K90,
sodium hydroxide/hydrochloric acid, and
water for injection.

In some aspects, the present disclosure contemplates a process of preparing the ophthalmic topical formulation of cyclosporine, said method comprising the steps of:

(1) melting the required amount of polyoxyl lipid,
(2) slowly adding cyclosporine to step (1) and substantially homogenizing the mixture,
(3) adding polyalkoxylated alcohol to step (2) and continue stirring until a uniform homogeneous solution is obtained,
(4) adding buffer system and tonicity agent to the solution obtained from step (3) and continue stirring to achieve a good dissolution,
(5) adding required amount of bioadhesive polymer to the solution of above step,
(6) adjusting the pH of the solution if required, and making up the final volume with water for injection; and
(7) aseptically filtering and filling the solution into unit dose vials.

In some aspects, the present disclosure contemplates melt-based methods for making cyclosporine-containing formulations, including the above-described formulations, said methods comprising:

melting hydrogenated 40 polyoxyl castor oil,
slowly adding cyclosporine thereto, and thereafter substantially mixing the ingredients,
adding octoxynol-40 (Igepal) to the resulting homogeneous mixture and stirring until substantially homogenous, and thereafter
adding this mixture to water for injection, then individually adding excipients (e.g., sodium phosphate monobasic, sodium phosphate dibasic, and sodium chloride) with stirring sufficient to achieve good dissolution of each.

An exemplary melt-based manufacturing process contemplated for use herein comprises the following steps:

Step 1: The requisite amount of HCO-40 is melted in a flask heated to about 60° C. with stirring. When liquefied, the required amount of cyclosporine is added and mixed until dissolved. The octoxynol-40 is then added and the entire solution is mixed until uniform
Step 2: The required amount of Water for Injection is charged into a stainless steel vessel and stirred until the temperature is 25° C.
Step 3: The contents from Step 1 are transferred to the stainless steel vessel and stirred until dissolved.
Step 4: The requisite amounts of Sodium Chloride and phosphate buffer are added to the stainless steel vessel, and the contents are mixed until dissolved.
Step 5: The required amount of Povidone is added to the vessel and stirred till dissolved.
Step 6: The pH of the solution in Step 5 is measured, adjusted (if necessary) and brought to the final volume with Water for Injection.
Step 7: The solution from Step 6 is aseptically filtered and aseptically filled into blow/fill/seal (BFS) unit dose vials with a nominal fill volume of 0.3 mL.
Step 8: The vials are packaged in strips of four (4) BFS units in heat sealed foil pouches.

In some aspects, the present disclosure contemplates process of preparing the ophthalmic topical formulation of cyclosporine, said method comprising the steps of:

(1) dissolving the required amounts of cyclosporine, polyalkoxylated alcohol and polyoxyl lipid in a suitable solvent,
(2) charging the solution obtained from step (1) to a suitable sized round bottom flask,
(3) removing the solvent by rotary evaporation until a thin film is obtained,
(4) adding and mixing required amount of water for injection to the flask containing film of step (3);
(5) adding buffer system and tonicity agent to the solution of step (4);
(6) adding required amount of bioadhesive polymer to the solution of above step,
(7) adjusting the pH of the solution if required, and making up the final volume with water for injection; and
(8) aseptically filtering and filling the solution into unit dose vials.

An exemplary solvent-based manufacturing process contemplated for use herein comprises the following steps:

(1) dissolving the required amounts of cyclosporine, octoxynol-40 and hydrogenated 40 polyoxyl castor oil in a suitable solvent,
(2) charging the solution obtained from step (1) to a suitable sized round bottom flask,
(3) removing the solvent by rotary evaporation until a thin film is obtained,
(4) adding and mixing required amount of water for injection to the flask containing film of step (3);
(5) adding phosphate buffer and sodium chloride to the solution of step (4);
(6) adding required amount of povidone to the solution of above step,
(7) adjusting the pH of the solution if required, and making up the final volume with water for injection; and
(8) aseptically filtering and filling the solution into unit dose vials.

The instant disclosure further relates to treating or preventing ocular diseases or disorders, for example by local administration of the formulations as described herein.

A patient or subject to be treated by any of the compositions or methods of the present disclosure can mean either a human or a non-human animal. In an embodiment, the present disclosure provides methods for the treatment of an ocular disease in a human patient in need thereof. In an embodiment, the present disclosure provides methods for the treatment of an inflammatory ocular disease in a human patient in need thereof. In another embodiment, the present disclosure provides methods for the treatment of an ocular disease in a veterinary patient in need thereof, including, but not limited to dogs, horses, cats, rabbits, gerbils, hamsters, rodents, birds, aquatic mammals, cattle, pigs, camelids, and other zoological animals.

In some embodiments of the compositions and methods disclosed herein, the cyclosporine further comprises one or more additional active ingredients, e.g., active agents selected from the group consisting of a resolvin or resolvin-like compound, a steroid (such as a corticosteroid), and the like. In some embodiments the additional active agent includes a resolvin. In some embodiments the additional active agent includes a corticosteroid. In some embodiments, the additional active agent includes a resolvin and a corticosteroid. In some embodiments, the additional active agent includes an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the additional active agent includes an antibiotic, for example one or more antibiotics selected from the group consisting of azythromycin, ciprofloxacin, ofloxacin, gatifloxacin, levofloxacin, moxifloxacin, besifloxacin, and levofloxacin; and a second of such agents is a resolvin such as described herein (including without limitation compound 1001). In some embodiments, the active agent includes two or more active agents and one of said active agents is an antiviral, for example one or more antivirals selected from the group consisting of ganciclovir, trifluridine, acyclovir, famciclovir, valacyclovir, penciclovir and cidofovir. In some embodiments, the active agent includes two or more active agents and one of the active agents is an antibiotic, for example one or more antivirals selected from the group consisting of ganciclovir, trifluridine, acyclovir, famciclovir, valacyclovir, penciclovir and cidofovir; and a second of the active agents is a resolvin such as described herein (including without limitation compound 1001).

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the terms "ocular disease," "ocular condition," "eye disease," and "eye condition" refer to diseases/conditions of the eye(s) that can be sight threatening, lead to eye discomfort, and may signal systemic health problems.

As used herein, the term "anterior segment disease" refers to all disorders that affect the eye surface, anterior chamber, iris and ciliary body and lens of the eye. The eye surface is composed of the cornea, conjunctiva, eyelids, lacrimal and meibomian glands, and the interconnecting nerves.

As used herein, the terms "posterior segment eye disease" and "back-of-the-eye disease" refer to all disorders that affect the posterior segment of the eye. A posterior eye disease is a disease which primarily affects a posterior ocular site such as choroid or sclera, vitreous, vitreous chamber, retina, optic nerve, and blood vessels and nerves which vascularize or innervate a posterior ocular site.

Accordingly, in another aspect, provided is a method treating or preventing an ocular disease or condition, that includes locally administering a formulation of any of the aspects or embodiments as disclosed herein. In some embodiments, the ocular disease is an anterior segment disease. In some embodiments, the ocular disease is a posterior segment disease. In some embodiments, the ocular disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker. In one embodiment, the ocular disease is dry eye. In one embodiment, the ocular disease is allergic conjunctivitis. In one embodiment the ocular disease is age-related macular degeneration (AMD). In one embodiment the ocular disease is diabetic retinopathy.

BRIEF DESCRIPTION OF THE FIGURE

FIG. 1 summarizes the results of the Schirmer Test with vehicle, formulation containing 0.05 wt % cyclosporine and 0.09 wt % cyclosporine.

DETAILED DESCRIPTION OF THE PREFERRED EMBODIMENTS

Active Agents

In accordance various aspects and embodiments of the methods and compositions provided herein, an active agent, when present in addition to cyclosporine, can be any agent capable of affecting a biological process. Active agents in addition to cyclosporine (the term active ingredient is used herein interchangably with the term active agent) include drugs, hormones, cytokines, toxins, therapeutic agents, vitamins and the like. In some embodiments an active agent in accordance with the aspects and embodiments disclosed herein is an agent capable of, or approved for, treating or preventing an disease or condition, for example in some embodiments an active agent is capable of, or approved for, treating or preventing an ocular disease or condition.

In some embodiments, the active agent in addition to cyclosporine is an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent is an antiviral, for example one or more antivirals selected from the group consisting of ganciclovir, trifluridine, acyclovir, famciclovir, valacyclovir, penciclovir and cidofovir.

In some embodiments of any of the aspects and embodiments disclosed herein, the active agent is cyclosporine A, an analog thereof, or a pharmaceutically acceptable salt thereof.

Cyclosporine, originally extracted from the soil fungus Potypaciadium infilatum, has a cyclic 11-amino acid structure and includes e.g. Cyclosporines A through I, such as Cyclosporine A, B, C, D and G. Cyclosporine binds to the cytosolic protein cyclophilin of immunocompetent lymphocytes, especially T-lymphocytes, forming a complex. The complex inhibits calcineurin, which under normal circumstances induces the transcription of interleukin-2 (IL-2). Cyclosporine also inhibits lymphokine production and interleukin release, leading to a reduced function of effector T-cells.

Ocular Diseases

In various aspects and embodiments the formulations as disclosed herein may be used to treat or prevent an ocular disease or disorder. Ocular diseases and disorders contemplated herein include anterior segment diseases and posterior segment diseases. Exemplary ocular diseases that may in certain embodiments be treated with formulations as disclosed herein include the following.

Dry eye syndrome (DES, Chronic dry eye, Keratitis sicca; Xerophthalmia; Keratoconjunctivitis sicca) can be defined as a condition that includes a variety of disorders that result in a loss of, or altered composition of, the natural tear film, which maintains the surface of the eye. Without this tear film, vision is impaired and patients may suffer severe ocular discomfort. DES can be caused by excessive tear evaporation or by a reduction of tear production in the lacrimal gland, which is the site of tear production. Though the exact causes of this condition are unknown, there is evidence supporting the link between reduced tear production and inflammation of one or more components of the lacrimal apparatus. Currently available medications for DES are leaving substantial room for more effective and better tolerated products.

DES may also be a manifestation of Sjogren's syndrome which is an autoimmune disorder in which the glands that produce tears and saliva are destroyed. This leads to dry mouth, decreased tearing, and other dry mucous membranes.

Noninfectious uveitis is a chronic inflammatory, putative Th1/Th17-mediated autoimmune disease associated with substantial visual morbidity and is potentially blinding. Blindness from uveitis usually does not occur from a single inflammatory episode; rather, cumulative damage results from recurrent episodes of inflammation. The inflammatory sequelae resulting in vision loss may include one or more of cystoid macular edema, cataracts, vitreous debris, glaucoma, macular pathology (scarring and atrophy), optic neuropathy, and retinal detachment.

Anterior uveitis (iritis) occurs in the front of the eye and is the most common form of uveitis. Par planitis is an inflammation of the pars plana, a narrow area between the iris and the choroid. This condition occurs more frequently in young men, but is usually not associated with another disease. Posterior uveitis (chondroitis) affects primarily the choroid; the back portion of the uveal tract. If the retina is also involved, it is called chorioretinitis. Posterior uveitis may occur in association with an autoimmune disease, or follow a systemic infection. In posterior uveitis, inflammation can last from months to years and may cause permanent vision damage, even with treatment.

Uveitis can cause vision impairment, ocular pain, and loss of vision. It is estimated that about 10% of new cases of blindness in the U.S. are caused by uveitis. Approximately 300,000 people suffer from uveitis in the U.S. alone, the majority of whom are affected by anterior uveitis. The only therapeutic class approved by the FDA for treatment of uveitis is corticosteroids, which are noted for multiple side effects, such as hypertension, hyperglycemia, and hypercholesterolemia, and in the eye, glaucoma and cataract formation.

Conjunctivitis (pink eye) describes a group of diseases that cause swelling, itching, burning, and redness of the conjunctiva, the protective membrane that lines the eyelids and covers exposed areas of the sclera, or white of the eye.

Keratitis is an inflammation of the cornea (clear portion in the front of the eye). Keratitis can be caused by an infection (bacterial, fungal, viral, parasite, etc.) or a non-infectious agent (e.g., certain types of auto-immune diseases are associated with a variety of non-infectious keratitises).

Keratoconjunctivitis refers to an inflammation of the cornea and conjunctiva.

Vernal keratoconjunctivitis (VKC) is a recurrent ocular inflammatory disease characterized by hard, elevated, cobblestone like bumps on the upper eyelid. There may also be swellings and thickening of the conjunctiva. The conjunctiva is the outermost membrane which lines the eyelids as well as the exposed parts of the eye, except for the cornea.

Atopic keratoconjunctivitis is the result of a condition called atopy. Atopy is a genetic condition whereby the immune system produces higher than normal antibodies in response to a given allergen.

Systemic immune mediated diseases such as cicatrizing conjunctivitis and other autoimmune disorders of the ocular surface represent a clinically heterogeneous group of conditions where acute and chronic autore active mechanisms can cause significant damage to the eye. When severe and affecting the epithelium and substantia propria of the conjunctiva, cicatrization can ensue, leading to significant mechanical alterations as a result of the fibrosis. These conditions, though generally infrequent, can be the cause of profound pathology and visual disability.

Blepharitis is a common condition that causes inflammation of the eyelids.

Scleritis is a serious inflammatory disease that affects the white outer coating of the eye, known as the sclera.

Age-related macular degeneration (AMD) is a disease associated with aging that gradually destroys sharp, central vision. AMD affects the macula, which is located at the center of the retina. AMD occurs in two forms: wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly. Dry AMD occurs when the light-sensitive cells in the macula slowly break down, gradually blurring central vision in the affected eye.

Diabetes can affect the eye in a number of ways. Diabetic retinopathy (DR) is a complication of diabetes that results from damage to the blood vessels of the light-sensitive tissue at the back of the eye (the retina). At first, diabetic retinopathy may cause no symptoms or only mild vision problems. Eventually, however, diabetic retinopathy can result in blindness. Diabetic macular edema (DME) is the swelling of the retina in diabetes mellitus due to leaking of fluid from blood vessels within the macula.

Ocular neovascularization is the abnormal or excessive formation of blood vessels in the eye. Ocular neovascularization has been shown in diabetic retinopathy and age-related macular degeneration (AMD).

Proliferative vitreoretinopathy (PVR) is scar tissue formation within the eye. "Proliferative" because cells proliferate and "vitreoretinopathy" because the problems involve the vitreous and retina. In PVR scar tissue forms in sheets on the retina which contract. This marked contraction pulls the retina toward the center of the eye and detaches and distorts the retina severely. PVR can occur both posteriorly and anteriorly with folding of the retina both anteriorly and circumferentially.

The cytomegalovirus (CMV) is related to the herpes virus and is present in almost everyone. When a person's immune system is suppressed because of disease (HIV), organ or bone marrow transplant, or chemotherapy, the CMV virus can cause damage and disease to the eye and the rest of the body. CMV affects the eye in about 30% of the cases by causing damage to the retina. This is called CMV retinitis.

Optic neuritis occurs when the optic nerve becomes inflamed and the myelin sheath becomes damaged or is destroyed. Nerve damage that occurs in the section of the optic nerve located behind the eye, is called retrobulbar neuritis, which is another term sometimes used for optic neuritis.

Also known as macular pucker, epiretinal membrane is a scar-tissue like membrane that forms over the macula. It typically progresses slowly and affects central vision by causing blurring and distortion. As it progresses, the pulling of the membrane on the macula may cause swelling.

In an embodiment, the compositions can be used for preventing transplant rejection of, for example, corneal allografts following transplantation. It is well known that in inflammation T-lymphocytes play a critical role in mediating rejection of foreign tissues. Prevention of rejection is of paramount importance in maintaining the health of transplanted corneas. Rejection may occur in any of the layers comprising the cornea, for example, the corneal epithelium, the corneal stroma or the corneal endothelium. The functioning of the cornea can be compromised following endothelial rejection. The endothelial layer serves to maintain the cornea in a compact state, acting as a pump by removing water from the corneal stroma. If the function of the endothelial layer is compromised, disorientation of collagen fibers can ensue, and transparency of the cornea can be lost. Human endothelial cells are non-replicative, and as a consequence, donor cell loss in the setting of rejection is irreversible and may lead to diminished graft function and survival. Thus, the goal of either prevention or treatment of rejection in corneal transplant recipients is to minimize endothelial cell loss. The compositions of the present disclosure can be used for the prevention of rejection following corneal allograft transplantation.

Additional Formulation Ingredients

The compositions of the present disclosure may also contain other components such as, but not limited to, additives, adjuvants, buffers, tonicity agents, bioadhesive polymers, and preservatives. In any of the compositions of this disclosure for topical to the eye, the mixtures are preferably formulated at about pH 5 to about pH 8. This pH range may be achieved by the addition of buffers to the composition as described in the examples. In an embodiment, the pH range in the composition in a formulation is about pH 6.6 to about pH 7.0. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The mixed micellar compositions of the present disclosure are stable in buffered aqueous solution. That is, there is no adverse interaction between the buffer and any other component that would cause the compositions to be unstable.

Tonicity agents include, for example, mannitol, sodium chloride, sodium nitrate, sodium sulfate, dextrose, xylitol or combinations thereof. These tonicity agents may be used to adjust the osmolality of the compositions. In an aspect, the osmolality of the formulation is adjusted to be in the range of about 250 to about 350 mOsmol/kg. In a preferred aspect, the osmolality of the formulation is adjusted to between about 280 to about 300 mOsmol/kg.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the calcineurin inhibitor, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose. In an embodiment, the sugars can be incorporated into a composition prior to hydrating the thin film (i.e. internally). In another embodiment, the sugars can be incorporated into a composition during the hydration step (i.e. externally). In an embodiment, an aqueous, clear, mixed micellar solution of the present disclosure includes additives such as sugars.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight. Bioadhesion systems have been used in dentistry, orthopedics, ophthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, a composition of the present disclosure includes at least one bioadhesive polymer. The bioadhesive polymer can enhance the viscosity of the composition and thereby increase residence time in the eye. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, povidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the compositions may optionally be preserved with any of many well-known preservatives, including benzyl alcohol with/without EDTA, benzalkonium chloride, chlorhexidine, Cosmocil®CQ, or Dowicil® 200. In certain embodiments, it may be desireable for a formulation as described herein to not include any preservatives. In this regard, preservatives may in some embodiments not be necessary or desirable in formulations included in single use containers. In other embodiments it may be advantageous to include preservatives, such as in certain embodiments in which the formulations are included in a multiuse container.

The ophthalmic compositions can be administered topically to the eye as biocompatible, aqueous, clear mixed micellar solutions. The compositions have the drugs incorporated and/or encapsulated in micelles which are dispersed in an aqueous medium.

Non-Limiting List of Exemplary Embodiments

In addition to the aspects and embodiments described and provided elsewhere in this disclosure, the following non-limiting list of particular embodiments are specifically contemplated.

1. An ophthalmic formulation, comprising 0.087-0.093 wt % cyclosporine, a polyoxyl lipid or fatty acid and a polyalkoxylated alcohol.
2. An ophthalmic formulation, comprising 0.087-0.093 wt % cyclosporine, and a n 40 polyoxyl lipid or fatty acid.
3. An ophthalmic formulation, comprising 0.087-0.093 wt % cyclosporine and a polyoxyl lipid or fatty acid; wherein said polyoxyl lipid or fatty acid is present in an amount equal to or greater than 0.5% of said formulation.
4. An ophthalmic formulation, comprising 0.087-0.093 wt % cyclosporine and a polyoxyl lipid or fatty acid; wherein said formulation comprises nanomicelles.
5. An ophthalmic formulation, comprising 0.087-0.093 wt % cyclosporine, 0.5-5% of one or more selected from the group consisting of HCO-40, HCO-60, HCO-80 and HCO-100; and about 0.01-0.1% octoxynol-40.
6. An ophthalmic formulation, comprising 0.087-0.093 wt % cyclosporine, 0.6-2% of one or more selected from the group consisting of HCO-40, HCO-60, HCO-80 and HCO-100; and about 0.02-0.1% octoxynol-40.
7. An ophthalmic formulation, comprising about 0.09% of cyclosporine, 0.5-5% of one or more selected from the group consisting of HCO-40, HCO-60, HCO-80 and HCO-100; and about 0.02-0.1% octoxynol-40.
8. An ophthalmic formulation, comprising 0.087-0.093 wt % cyclosporine, 0.6-4% of one or more polyoxyl lipids selected from the group consisting of HCO-40, HCO-60, HCO-80 and HCO-100; and about 0.02-0.1% octoxynol-40.
9. An ophthalmic formulation, comprising 0.087-0.093 wt % cyclosporine, 0.7-4% of polyoxyl lipids or fatty acids; and about 0.02-0.1% octoxynol-40.
10. An ophthalmic formulation, comprising 0.087-0.093 wt % cyclosporine, 0.8-4% of polyoxyl lipids or fatty acids; and about 0.02-0.1% octoxynol-40; wherein the formulation comprises nanomicelles.
11. An ophthalmic formulation, comprising 0.087-0.093 wt % cyclosporine, 0.9-4% of polyoxyl lipids or fatty acids; and about 0.02-0.1% octoxynol-40; wherein the formulation comprises nanomicelles.
12. An ophthalmic formulation, comprising 0.087-0.093 wt % cyclosporine, about 1% of one or more selected from the group consisting of HCO-40, HCO-60, HCO-80 and HCO-100; and about 0.02-0.1% octoxynol-40.
13. An ophthalmic formulation, comprising 0.087-0.093 wt % cyclosporine, about 1% of HCO-60 and about 0.02-0.1% octoxynol-40.
14. An ophthalmic formulation, comprising 0.087-0.093 wt % cyclosporine, 0.5-4% of one or more selected from the group consisting of HCO-40, HCO-60, HCO-80 and HCO-100; and about 0.05% octoxynol-40.
15. An ophthalmic formulation, comprising 0.087-0.093 wt % cyclosporine, 0.5-4% of one or more selected from the group consisting of HCO-40, HCO-60, HCO-80 and HCO-100; and about 0.01% octoxynol-40.
16. An ophthalmic formulation, comprising about 0.09% of cyclosporine, 0.5-4% of one or more selected from the group consisting of HCO-40, HCO-60, HCO-80 and HCO-100; and about 0.05% octoxynol-40.
17. An ophthalmic formulation, comprising 0.087-0.093 wt % cyclosporine, 0.6-2% of one or more polyoxyl lipids selected from the group consisting of HCO-40, HCO-60, HCO-80 and HCO-100; and about 0.05% octoxynol-40.
18. An ophthalmic formulation, comprising 0.087-0.093 wt % cyclosporine, 0.6-2% of polyoxyl lipids or fatty acids; and about 0.05% octoxynol-40.
19. An ophthalmic formulation, comprising 0.087-0.093 wt % cyclosporine, 0.6-2% of polyoxyl lipids or fatty acids; and about 0.05% octoxynol-40; wherein the formulation comprises nanomicelles.
20. An ophthalmic formulation, comprising 0.087-0.093 wt % cyclosporine, 0.6-2% of polyoxyl lipids or fatty acids; and about 0.05% octoxynol-40; wherein the formulation comprises nanomicelles.
21. An ophthalmic formulation, comprising 0.087-0.093 wt % cyclosporine, about 1% of one or more selected from the group consisting of HCO-40, HCO-60, HCO-80 and HCO-100; and about 0.05% octoxynol-40.
22. An ophthalmic formulation, comprising 0.087-0.093 wt % cyclosporine, about 1% of HCO-60 and about 0.05% octoxynol-40.
23. The formulation of any of the preceding embodiments, wherein said polyoxyl lipid or fatty acid is between 0.6 and 2% by weight of said formulation.
24. The formulation of any of the preceding embodiments, wherein said polyoxyl lipid or fatty acid is between 0.8 and 2% by weight of said formulation.
25. The formulation of any of the preceding embodiments, wherein said polyoxyl lipid or fatty acid is between 0.9 and 1.5% by weight of said formulation.
26. The formulation of any of the preceding embodiments, wherein said polyoxyl lipid or fatty acid is between 1 and 1.5% by weight of said formulation.
27. The formulation of any of the preceding embodiments, wherein said polyoxyl lipid or fatty acid is between 0.5 and 5% by weight of said formulation.
28. The formulation of any of the preceding embodiments, wherein said polyoxyl lipid or fatty acid is between 0.6 and 5% by weight of said formulation.
29. The formulation of any of the preceding embodiments, wherein said polyoxyl lipid or fatty acid is between 0.6 and 4% by weight of said formulation.
30. The formulation of any of the preceding embodiments, wherein said polyoxyl lipid or fatty acid is between 0.6 and 3% by weight of said formulation.
31. The formulation of any of the preceding embodiments, wherein said polyoxyl lipid or fatty acid is between 0.6 and 2% by weight of said formulation.

32. The formulation of any of the preceding embodiments, wherein said polyoxyl lipid or fatty acid is between 0.6 and 1% by weight of said formulation.
33. The formulation of any of the preceding embodiments, wherein said polyoxyl lipid or fatty acid is between 0.8 and 5% by weight of said formulation.
34. The formulation of any of the preceding embodiments, wherein said polyoxyl lipid or fatty acid is between 0.8 and 4% by weight of said formulation.
35. The formulation of any of the preceding embodiments, wherein said polyoxyl lipid or fatty acid is between 0.8 and 3% by weight of said formulation.
36. The formulation of any of the preceding embodiments, wherein said polyoxyl lipid or fatty acid is between 0.8 and 2% by weight of said formulation.
37. The formulation of any of the preceding embodiments, wherein said polyoxyl lipid or fatty acid is between 0.9 and 2% by weight of said formulation.
38. The formulation of any of the preceding embodiments, wherein said polyoxyl lipid or fatty acid is between 0.9 and 1.5% by weight of said formulation.
39. The formulation of any of the preceding embodiments, wherein said polyoxyl lipid or fatty acid is about 1% by weight of said formulation.
40. The formulation of any of the preceding embodiments, wherein said polyoxyl lipid or fatty acid is greater than about 0.6% by weight of said formulation.
41. The formulation of any of the preceding embodiments, wherein said polyoxyl lipid or fatty acid is greater than about 0.7% by weight of said formulation.
42. The formulation of any of the preceding embodiments, wherein said polyoxyl lipid or fatty acid is greater than about 0.8% by weight of said formulation.
43. The formulation of any of the preceding embodiments, wherein said polyoxyl lipid or fatty acid is greater than about 0.9% by weight of said formulation.
44. The formulation of any of the preceding embodiments, wherein said polyoxyl lipid or fatty acid is greater than about 1% by weight of said formulation.
45. The formulation of any of the preceding embodiments, wherein said polyalkoxylated alcohol if present is between 0.005 and 4% by weight of said formulation.
46. The formulation of any of the preceding embodiments, wherein said polyalkoxylated alcohol if present is between 0.005 and 3% by weight of said formulation.
47. The formulation of any of the preceding embodiments, wherein said polyalkoxylated alcohol if present is between 0.005 and 2% by weight of said formulation.
48. The formulation of any of the preceding embodiments, wherein said polyalkoxylated alcohol if present is between 0.005 and 1% by weight of said formulation.
49. The formulation of any of the preceding embodiments, wherein said polyalkoxylated alcohol if present is between 0.005 and 0.5% by weight of said formulation.
50. The formulation of any of the preceding embodiments, wherein said polyalkoxylated alcohol if present is between 0.005 and 0.1% by weight of said formulation.
51. The formulation of any of the preceding embodiments, wherein said polyalkoxylated alcohol if present is between 0.005 and 0.05% by weight of said formulation.
52. The formulation of any of the preceding embodiments, wherein said polyalkoxylated alcohol if present is between 0.008 and 0.02% by weight of said formulation.
53. The formulation of any of the preceding embodiments, wherein said polyalkoxylated alcohol if present is about 0.05% by weight of said formulation.
54. The formulation of any of the preceding embodiments, wherein said polyoxyl lipid or fatty acid is a polyoxyl castor oil.
55. The formulation of any of the preceding embodiments, wherein said polyoxyl lipid or fatty acid is one or more selected from HCO-60, HCO-80 or HCO-100.
56. The formulation of any of the preceding embodiments, wherein said polyoxyl lipid or fatty acid is HCO-60.
57. The formulation of any of the preceding embodiments, wherein said active agent comprises a combination of two different agents.
58. The formulation of any of the preceding embodiments, wherein the active agent comprises two or more active agents selected from the group consisting of a resolvin or resolvin-like compound, a steroid (such as a corticosteroid), cyclosporine A, and voclosporin.
59. The formulation of any of the preceding embodiments, wherein the active agent further comprises a resolvin and a corticosteroid.
60. The formulation of any of the preceding embodiments, wherein the active agent comprises cyclosporine A and a corticosteroid.
61. The formulation of any of the preceding embodiments, wherein the active agent comprises a resolvin, cyclosporine A and a corticosteroid.
62. The formulation of any of the preceding embodiments, wherein said formulation does not include preservatives.
63. The formulation of any of the preceding embodiments, wherein said formulation does not include benzyl alcohol with/without EDTA, benzalkonium chloride, chlorhexidine, Cosmocil®CQ, or Dowicil®0.200.
64. A method of treating or preventing an ocular disease or condition, said method comprising topically administering a formulation of any of the preceding embodiments.
65. A method of treating or preventing an ocular disease or condition, said method comprising topically administering a formulation of any of the preceding embodiments; wherein said disease is an anterior segment disease.
66. A method of treating or preventing an ocular disease or condition, said method comprising topically administering a formulation of any of the preceding embodiments; wherein said disease is an posterior segment disease.
67. A method of treating or preventing an ocular disease or condition, said method comprising topically administering a formulation of any of the preceding embodiments; wherein said disease is one or more selected from the group consisting of dry eye syndrome, Sjogren's syndrome, uveitis, anterior uveitis (iritis), chorioretinitis, posterior uveitis, conjunctivitis, allergic conjunctivitis, keratitis, keratoconjunctivitis, vernal keratoconjunctivitis (VKC), atopic keratoconjunctivitis, systemic immune mediated diseases such as cicatrizing conjunctivitis and other autoimmune disorders of the ocular surface, blepharitis, scleritis, age-related macular degeneration (AMD), diabetic retinopathy (DR), diabetic macular edema (DME), ocular neovascularization, age-related macular degeneration (ARMD), proliferative vitreoretinopathy (PVR), cytomegalovirus (CMV) retinitis, optic neuritis, retrobulbar neuritis, and macular pucker.

68. A method of treating or preventing an ocular disease or condition, said method comprising topically administering a formulation of any of the preceding embodiments; wherein said disease is dry eye syndrome.
69. A method of treating or preventing an ocular disease or condition, said method comprising topically administering a formulation of any of the preceding embodiments; wherein said disease is allergic conjunctivitis.
70. A method of treating or preventing an ocular disease or condition, said method comprising topically administering a formulation of any of the preceding embodiments; wherein said disease is age-related macular degeneration (AMD).

The following examples are provided to further illustrate aspects of the invention. These examples are non-limiting and should not be construed as limiting any aspect of the invention.

EXAMPLE 1

Preparation of Mixed Nanomicellar Cyclosporine-Containing Formulations

Mixed nanomicellar formulations cyclosporine are prepared as follows:

- melting hydrogenated 40 polyoxyl castor oil,
- slowly adding cyclosporine thereto, and thereafter substantially homogenizing the ingredients,
- adding octoxynol-40 to the resulting homogeneous mixture and stirring until substantially homogenous, and thereafter
- individually adding excipients (e.g., sodium phosphate monobasic, sodium phosphate dibasic, and sodium chloride) with stirring sufficient to achieve good dissolution of each.

The prepared formulations are subjected to various tests such as entrapment efficiency, loading efficiency, mixed nanomicellar size and polydispersity index.

Mixed Nanomicellar Size and Polydispersity Index:

The formulation size and polydispersity index are determined with Zetasizer, Malvern Instruments, NJ. In brief, approximately 1 ml of each formulation was transferred to a cuvette and placed in the instrument. A laser beam of light was used to determine the mixed nanomicellar size. Nanomicelles contemplated by the present disclosure typically have a particle size in the range of about 1-100 nm; in some embodiments, the particle size falls in the range of about 5-50 nm; in some embodiments, the particle size falls in the range of about 10-40 nm; in some embodiments, the particle size is about 15 nm.

Entrapment Efficiency:

To determine the entrapment efficiency of the formulation, all the prepared formulations are subjected to an entrapment efficiency test. Briefly, formulations are vortex mixed for homogeneity and 1 mL is transferred to a fresh (1.5 mL) eppendorf tube. Each formulation is lyophilized to obtain a solid at the bottom of the eppendorf tube. The obtained solid is suspended in 1 mL of organic solvent (diethyl ether) to generate reverse micelles and release the drug into the external organic solvent. The organic solvent is evaporated overnight in speed vacuum The resultant reversed micelles are resuspended in 1 mL of 2-propanol (dilution factor was taken into account) and further diluted to determine the concentration of cyclosporine entrapped in each micellar preparation with HPLC. The entrapment efficiency of the formulation is calculated with the following formula (wherein MNF=Mixed Nanomicellar Formulation):

$$\text{Entrapment efficiency} = \frac{(\text{amount of drug quantified in } MNF)}{\text{Amount of drug added in the } MNF} \times 100$$

Drug Quantification by an HPLC Method:

In vitro analysis of cyclosporine is performed by a reversed phase high performance liquid chromatography (RP-HPLC) method with a Shimadzu HPLC pump (Shimadzu, Shimadzu Scientific instruments, Columbia, MD), Alcott autosampler (model 718 AL), Shimadzu UV/Visible detector (Shimadzu, SPD-20A/20AV, USA), ODS column (5 μm, 150×4.6 mm) thermostated at 400±1 C and Hewlett Packard HPLC integrator (Hewlett Packard, Palo Alto, CA). The mobile phase is comprised of methanol (MeOH), water and trifluoroacetic acid (TFA) (70:30:0.05% v/v) which is set at a flow rate of 0.5 mL/min. Detection wavelength is set at 272 nm The sample tray temperature is maintained at 4° C. Calibration curve (0.5 to 5 μg/mL) for cyclosporin is prepared by making appropriate dilutions from the stock solution in 2-propanol. An injection volume of 10 μl is injected into the HPLC column for analysis. All the standards and samples prepared are stored at 4° C. before and during the analysis.

EXAMPLE 2

Preparation of Mixed Nanomicellar Cyclosporine-containing Formulation Using Solvent-Based Method or Melt-Based Method Mixed nanomicellar formulation encapsulating cyclosporine is prepared by solvent evaporation method in two steps:

- Compounding of the bulk ophthalmic solution; and
- Filling of the bulk ophthalmic solution into blow/fill/seal (BFS) unit doses with subsequent packaging of strips of four (4) BFS units into individual foil pouches.

An exemplary solvent-based manufacturing process contemplated for use herein is described in more detail as follows:

- Step 1: The requisite amounts of cyclosporine, octoxynol-40, and HCO-40 are dissolved in ethanol and charged to a suitable size round bottom flask. The flask is attached to a rotary evaporator and rotation is initiated to mix the contents of the flask.
- Step 2: The ethanol is removed by rotary evaporation until a thin film is obtained.
- Step 3: The requisite amount of Water for Injection is charged to the flask containing the film of Step 2, and the contents are dissolved by rotational (laminar flow) mixing.
- Step 4: The requisite amounts of Sodium Chloride and previously prepared phosphate buffer are added to a stainless steel vessel, and the contents are mixed.
- Step 5: The contents from Step 3 are transferred to the tank containing the buffer and stirred until dissolved.
- Step 6: The required amount of Povidone is added to the tank and stirred until dissolved.
- Step 7: The pH of the solution in Step 6 is measured, adjusted (if necessary) and brought to the final volume with Water for Injection.

Step 8: The solution from Step 7 is aseptically filtered and aseptically filled into blow/fill/seal (BFS) unit dose vials with a nominal fill volume of 0.25 mL.

Step 9: The vials are packaged in strips of four (4) BFS units in heat sealed foil pouches.

An exemplary melt-based manufacturing process contemplated for use herein is described in more detail as follows:

Step 1: The requisite amount of HCO-40 is melted in a flask heated to about 60° C. with stirring. When liquefied, the required amount of cyclosporine is added and mixed until dissolved. The octoxynol-40 is then added and the entire solution is mixed until uniform Step 2: The required amount of Water for Injection is charged into a stainless steel vessel and stirred until the temperature is 25° C.

Step 3: The contents from Step 1 are transferred to the stainless steel vessel and stirred until dissolved.

Step 4: The requisite amounts of Sodium Chloride and phosphate buffer are added to the stainless steel vessel, and the contents are mixed until dissolved.

Step 5: The required amount of Povidone is added to the vessel and stirred until dissolved.

Step 6: The pH of the solution in Step 5 is measured, adjusted (if necessary) and brought to the final volume with Water for Injection.

Step 7: The solution from Step 6 is aseptically filtered and aseptically filled into blow/fill/seal (BFS) unit dose vials with a nominal fill volume of 0.3 mL.

Step 8: The vials are packaged in strips of four (4) BFS units in heat sealed foil pouches.

EXAMPLE 3

Preparation of Mixed Nanomicellar Cyclosporine-Containing Formulation Using Ethanol Solvent Evaporation Method Mixed nanomicellar formulation encapsulating cyclosporin is prepared by solvent evaporation method in two steps:

Compounding of the bulk ophthalmic solution; and

Filling of the bulk ophthalmic solution into blow/fill/seal (BFS) unit doses with subsequent packaging of strips of four (4) BFS units into individual foil pouches.

The manufacturing process employed herein is described in more detail as follows:

Step 1: The requisite amounts of cyclosporine, octoxynol-40, and Vitamin E Polyethylene Glycol Succinate are dissolved in ethanol and charged to a suitable size round bottom flask. The flask is attached to a rotary evaporator and rotation is initiated to mix the contents of the flask.

Step 2: The ethanol is removed by rotary evaporation until a waxy solid is obtained.

Step 3: The requisite amount of Water for Injection is charged to the flask containing the waxy residue in Step 2, and the contents are dissolved by rotational (laminar flow) mixing.

Step 4: The contents from Step 3 are transferred to a stainless steel vessel containing the required amount of Povidone solution and the contents are mixed until uniform Step 5: The requisite amounts of Sodium Chloride and previously prepared phosphate buffer are added to the solution in Step 4, and the contents are mixed.

Step 6: The pH of the solution in Step 5 is measured, adjusted (if necessary) and brought to the final volume with Water for Injection.

Step 7: The solution from Step 6 is aseptically filtered and aseptically filled into blow/fill/seal (BFS) unit dose vials with a nominal fill volume of 0.25 mL.

Step 8: The vials are packaged in strips of four (4) BFS units in heat sealed foil pouches.

EXAMPLE 4

Preparation of Mixed Nanomicellar Cyclosporine-Containing Formulations Using an Alternative Order of Addition Melt-Based Method Step 1: The requisite amount of HCO-40 is melted in a flask heated to about 60° C. with stirring. When liquefied, the required amount of cyclosporine is added and mixed until dissolved and uniform Step 2: The required amount of Octoxynol-40 is heated to about 60° C. and when liquefied, is added to the cyclosporine HCO-40 mixture.

Step 3: The required amount of Water for Injection at about 25° C. is charged into the flask containing the dissolved cyclosporine and stirred until dissolved.

Step 4: The requisite amounts of Sodium Chloride and phosphate buffer are added to the flask, and the contents are mixed.

Step 5: PVP-K90 is weighed, added to the solution and mixed until dissolved.

Step 6: The pH of the solution in Step 5 is measured, adjusted (if necessary) and brought to the final volume with Water for Injection.

EXAMPLE 5

Any of the protocols described herein can be carried out with the following reagents:

0.09 wt % cyclosporine,
1.0 wt % hydrogenated 40 polyoxyl castor oil, and
0.05 wt % octoxynol-40 (Igepal),
0.405 wt % sodium phosphate monobasic, and optionally
0.465 wt % sodium phosphate dibasic,
0.05 wt % sodium chloride,
0.3 wt % povidone K90, and
water for injection.

A randomized, multicenter, double-masked, vehicle-controlled, dose-ranging study was designed to evaluate 2 concentrations of OTX-101 ophthalmic solution, 0.09% and 0.05%, against vehicle in approximately 420 subjects with keratoconjunctivitis sicca (KCS). Subjects who met eligibility criteria at Screening (patient-reported history of KCS for 6 months, clinical diagnosis of bilateral KCS, lissamine green staining score of ≥3 to ≤9, and global symptom score ≥40 based on a modified "Symptom Assessment iN Dry Eye" (SANDE) questionnaire) entered a run-on period with vehicle administered topically twice daily (BID) to both eyes for 14 days. Following the run-in, subjects who continued to meet the lissamine green staining score and global symptom score inclusion criteria in at least one eye were randomized into 1 of 3 treatment groups and received treatment for 12 weeks (84 days):

OTX-101 0.05% 1 drop in both eyes BID,
OTX-101 0.09% 1 drop in both eyes BID, and
Vehicle 1 drop in both eyes BID.

Subject symptoms were assessed with the SANDE questionnaire, subject signs were assessed with lissamine green conjunctiva! staining, corneal fluorescein staining, Schirmer's test (unanesthetized), and tear break-up time, and subject satisfaction with treatment was assessed using a 5-point ordinal scale. Safety was assessed by Snellen visual acuity (VA), slit-lamp examination, intraocular pressure (IOP) tonometry, dilated ophthalmoscopy/fundus examination, adverse event (AE) collection, and concomitant medication review. Safety and efficacy evaluations were conducted at study visits on Days 14, 28, 42, 56, and 84. Both eyes were assessed at each visit.

The results are presented in FIG. 1, where it can be seen that formulations according to the present disclosure (containing 0.09 wt % cyclosporine) are substantially more effective than placebo or formulations containing only 0.05 wt % cyclosporine.

Formulations according to the present disclosure containing 0.09 wt % cyclosporine were not only superior to vehicle with respect to the Schirmer's test ($p=0.007$), such formulations were also superior to vehicle with respect to conjunctiva! staining (co-primary, $p=0.008$) and corneal staining ($p<0.001$). Formulations of the present disclosure (containing 0.09 wt % cyclosporine) showed clinically meaningful improvement in tear production in the subjects with ≥10 mm increase in Schirmer's test score from baseline based on data for both eyes.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

The invention claimed is:

1. A method of treating an inflammatory ocular disease in a subject, comprising administering twice daily for at least 12 weeks to both eyes of the subject, an ophthalmic aqueous topical formulation consisting of 0.09 wt % cyclosporine; about 1.0 wt % hydrogenated 40 polyoxyl castor oil; about 0.05 wt % octoxynol-40; about 0.05 wt % sodium chloride; about 0.3 wt % povidone; about 0.20-0.405 wt % sodium phosphate monobasic; about 0.23-0.465 wt % sodium phosphate dibasic; and sodium hydroxide and/or hydrochloric acid, wherein pH of the formulation is about 5 to about 8,
wherein the subject has:
i) a history of keratoconjunctivitis sicca (KCS) for at least 6 months; and
ii) a clinical diagnosis of bilaterial KCS.

2. The method of claim 1, wherein the pH of the formulation is about 6.6 to about 7.0.

3. The method of claim 1, wherein the cyclosporine is present in one or more nanomicelles in the formulation.

4. The method of claim 3, wherein the nanomicelles have a particle size of about 10 nm to about 40 nm.

5. The method of claim 3, wherein the nanomicelles have a particle size of about 15 nm.

6. A unit dose vial containing about 0.25 mL or about 0.3 mL of an ophthalmic aqueous topical formulation consisting of:
0.087-0.093 wt % cyclosporine,
about 1.0 wt % hydrogenated 40 polyoxyl castor oil,
about 0.05 wt % octoxynol-40,
about 0.3 wt % povidone,
about 0.05 wt % sodium chloride,
about 0.20-0.405 wt % sodium phosphate monobasic,
about 0.23-0.465 wt % sodium phosphate dibasic,
sodium
hydroxide/hydrochloric acid, and
water,
wherein pH of the formulation is about 5 to about 8.

7. The unit dose vial of claim 6, wherein the cyclosporine is about 0.09 wt % of the formulation.

8. The unit dose vial of claim 6, wherein the cyclosporine is present in one or more nanomicelles in the formulation.

9. The unit dose vial of claim 8, wherein the nanomicelles have a particle size of about 10 nm to about 40 nm.

10. The unit dose vial of claim 8, wherein the nanomicelles have a particle size of about 15 nm.

11. The unit dose vial of claim 6, wherein the pH of the formulation is about 6.6 to about 7.0.

12. A process of preparing an ophthalmic aqueous topical formulation comprising 0.09 wt % cyclosporine, about 1.0 wt % hydrogenated 40 polyoxyl castor oil, about 0.05 wt % octoxynol-40, about 0.3 wt % povidone, about 0.05 wt % sodium chloride, about 0.20-0.405 wt % sodium phosphate monobasic, and about 0.23-0.465 wt % sodium phosphate dibasic, the process comprising:

(1) melting the hydrogenated 40 polyoxyl castor oil;

(2) slowing adding the cyclosporine to the melted hydrogenated 40 polyoxyl castor oil of step (1) to form a mixture, and substantially homogenizing the mixture;

(3) adding the octoxynol-40 to the mixture of step (2), and continue stirring until a uniform homogenous solution is obtained;

(4) adding the sodium phosphate monobasic, sodium phosphate dibasic, and sodium chloride to the solution of step (3), and continue stirring to achieve dissolution to form a solution of step (4);

(5) adding the povidone to the solution of step (4) to form a solution of step (5);

(6) adjusting pH of the solution of step (5) to about 5 to about 8, and adding water to form a solution of step (6); and (7) aseptically filtering and filling the solution of step (6) into unit dose vials.

13. A process of preparing an ophthalmic aqueous topical formulation comprising 0.09 wt % cyclosporine, about 1.0 wt % hydrogenated 40 polyoxyl castor oil, about 0.05 wt % octoxynol-40, about 0.3 wt % povidone, about 0.05 wt % sodium chloride, about 0.20-0.405 wt % sodium phosphate monobasic, and about 0.23-0.465 wt % sodium phosphate dibasic, the process comprising:

(1) dissolving the cyclosporine, octoxynol-40, and hydrogenated 40 polyoxyl castor oil in a solvent to form a solution of step (1);

(2) removing the solvent until a thin film is obtained;

(3) adding water to the film of step (2) to form a solution of step (3);

(4) adding the sodium phosphate monobasic, sodium phosphate dibasic, and sodium chloride to the solution of step (3) to form a solution of step (4);

(5) adding povidone to the solution of step (4) to form a solution of step (5);

(6) adjusting pH of the solution of step (4) to about 5 to about 8, and adding water to form a solution of step (6); and (7) aseptically filtering and filling the solution of step (6) into unit dose vials.

14. The process of claim 13, wherein step (2) comprises charging the solution of step (1) to a round bottom flask, and removing the solvent by rotary evaporation.

* * * * *